Figure 1:
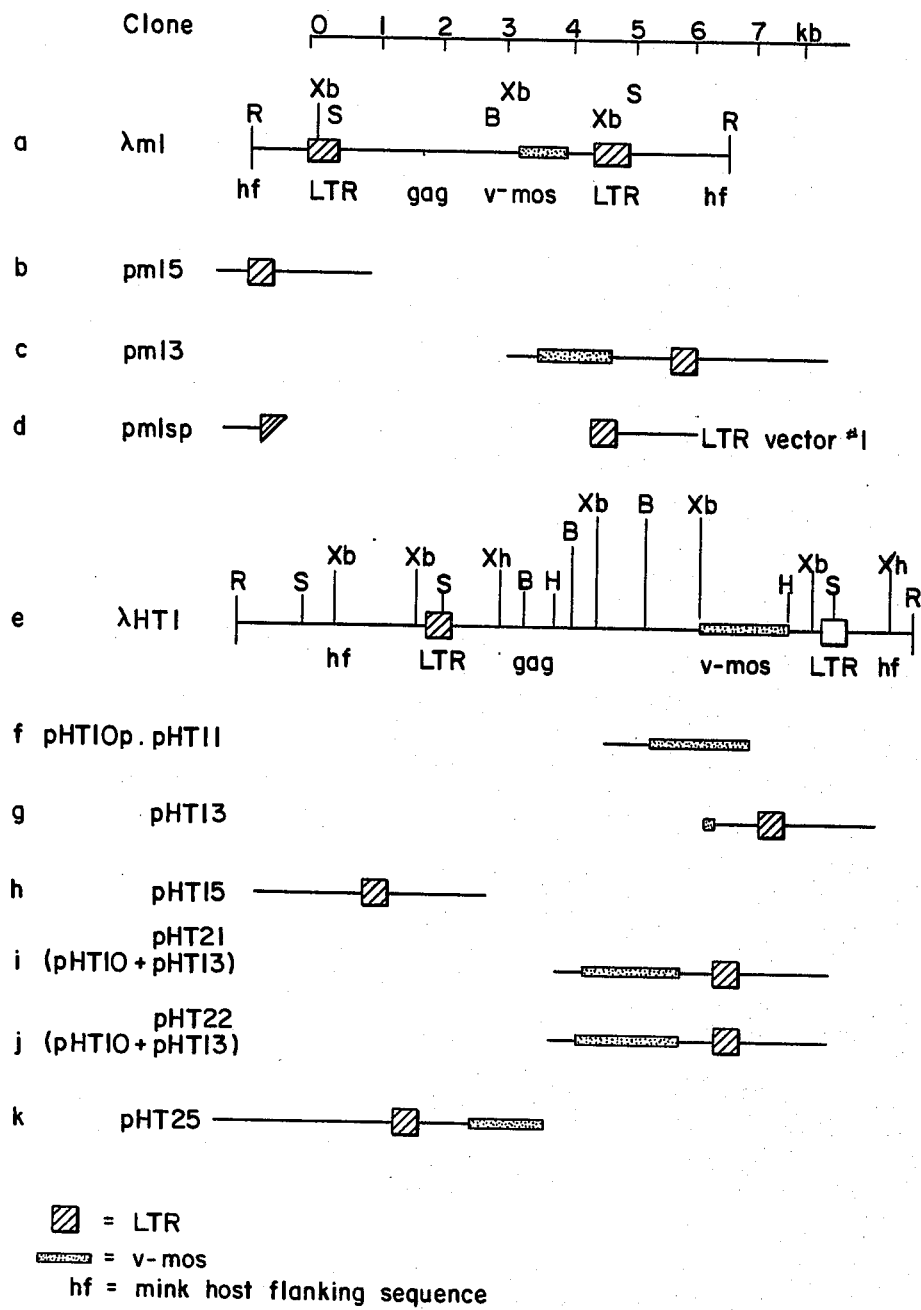

United States Patent [19]

Vande Woude et al.

[11] 4,405,712
[45] Sep. 20, 1983

[54] LTR-VECTORS

[75] Inventors: George F. Vande Woude, Berryville, Va.; William L. McClements, Silver Spring, Md.; Marianne K. Oskarsson, Bethesda, Md.; Donald G. Blair, Kensington, Md.

[73] Assignee: The United States of America as represented by the Department of Health and Human Services, Washington, D.C.

[21] Appl. No.: 279,443

[22] Filed: Jul. 1, 1981

[51] Int. Cl.$^3$ .................. C12Q 1/70; C12P 21/00; C12P 21/02; C12N 15/00; C12N 5/00; C12N 1/00; C12N 7/00
[52] U.S. Cl. .................. 435/5; 435/68; 435/70; 435/172; 435/240; 435/317; 435/235
[58] Field of Search .................. 435/5, 172, 235, 239

[56] References Cited

U.S. PATENT DOCUMENTS 4,237,224 12/1980 Cohen et al. .................. 435/172
4,332,893 6/1982 Rosenberg .................. 435/235

OTHER PUBLICATIONS

Luria et al., *General Virology*, 3rd Edition, John Wiley & Sons, New York, 1978, pp. 379–389.
Wei et al., J. Virol. 39, 935 (1981) in Chem. Abstr. 95:146932 (1981).
Wigler et al., Cell 11, 223 (1977).
McClements et al., Cold Spring Harbor Laboratory Symposium 45 (1981).
Blair et al., Proc. Natl. Acad. Sci., vol. 77, Jun. 1980, pp. 3504–3508.
Blair et al., Science, vol. 212, May 1981, pp. 941–942.
Oskarsson et al, Science, 207:Mar. 1980, pp. 1222–1224.
Dhar et al., Proc. Natl. Acad. Sci., vol. 77, Jul. 1980, pp. 3937–3941.
Vande Woude et al., Cold Spring Harbor Symposium on Quantitative Biology, vol. XLIV, 1980, pp. 735–745.

*Primary Examiner*—Alvin E. Tanenholtz
*Assistant Examiner*—James Martinell
*Attorney, Agent, or Firm*—John S. Roberts, Jr.

[57] ABSTRACT

The production of vectors composed of portions of retrovirus, particularly of Moloney sarcoma virus DNA including the "LTR" sequence which can activate genes and additional viral sequences which can "rescue" these genes into a replicating virus particle.

10 Claims, 2 Drawing Figures

MODEL SYSTEM FOR RESCUE

MODEL SYSTEM FOR RESCUE

LTR-VECTORS

PHYSICAL AND BIOLOGICAL CONTAINMENT

This work was performed under physical and biological containment (P2-EK2) as specified by the National Institutes of Health Guidelines for Recombinant DNA Research.

A deposit of the LTR vectors pm1sp, pRC1, and pRC3, (designated Vector 1, Vector 2, Vector 3, respectively) (in pBr322) has been placed with and made available to the public at the American Type Culture Collection, Rockville, Md., U.S.A., and have been assigned ATCC Nos. 31893, 31894, and 31895, respectively.

LTR vector No. 1 (pm1sp) has ATCC No. 31893. LTR vector No. 2 (pRC1) has ATCC No. 31894. LTR vector No. 3 (pRC3) has ATCC No. 31895.

PRIOR ART STATEMENT

Oskarsson, M., et al. Science 207 March 1980, pp. 1222-1224.

Dhar, et al. Proc. Nat'l. Acad. Sci. Vol. 77, July 1980, pp. 3937-3941.

Vande Woude, G., et al. Cold Spring Harbor Symposium on Quantitative Biology, Vol. XLIV, 1980, pp. 735-745.

McClements, W. L., et al. Cold Spring Harbor Laboratory Symposium 45 (1981).

Blair et al., Proc. Nat'l Acad. Sci. 77, June 1980, pp. 3504-3508.

Blair et al., Science 212, May 1981, pp. 941-942.

The above articles broadly discuss work on retroviruses.

U.S. Pat. No. 4,237,224 is incorporated herein by reference for general background on cloning, i.e., recombinant techniques.

BACKGROUND OF THE INVENTION

Procaryotic viruses have been relatively studied and used as cloning vectors for the past decade. Unfortunately, procaryotes do not provide sufficient cellular mechanisms for the expression of many gene products of viral interest for eukaroytic cells.

A readily identifiable phenotype is of primary concern for identifying a cloned gene. Thus, a vector system is required that allows expression of the cloned sequence.

Furthermore, cloning a specific gene requires the purification and amplification of that specific entity from an environment of many genes. One powerful purification and amplification lies in "rescue." By this is meant that the gene of interest can be isolated from a background of many genes by incorporation into an infectious virus that can be purified by standard microbial techniques. The vector is linked to the fragmented genomic DNA and introduced into cells that can express the desired phenotype.

After several rounds of replication, the expressed genome, the genome of interest, is an abundant product. The genome, appropriately tested, will show that phenotype that characterizes it. This screening technique cannot be used in bacterial environments which lack functions of eukaryotic cells.

SUMMARY OF THE INVENTION

The present invention describes retrovirus LTR vectors and in particular model systems involving LTR vectors derived from ml Moloney sarcoma virus. Vectors of pm1sp, pRC1, and pRC3 are given in detail.

The retrovirus LTR vectors activate the expression of any gene and, by virtue of the phenotype of the gene, screening and identification of the gene. The LTR vector can be linked to the gene of interest by conventional recombinant techniques and serves as a marker for identification and cloning of the gene by standard recombinant DNA cloning procedures. Particular vectors, pRC1 and pRC3, for example, which contain LTR and additional viral sequences necessary for the generation of virus make possible the cloning of a gene into a replicating virus, thereby rescuing the gene from a background of many genes and permitting high yield amplification. The process permits for the cloning of very complex genes, since it removes the intervening sequences.

An appropriate viral vector, one that provides information for making an infectious virus particle, allows the vector plus the linked sequences to be packaged into a virus particle when a helper-virus is superinfected into the cells expressing the gene of interest. This "rescue" of the gene of interest provides an absolute purification step.

The present invention provides for vectors composed of a particular retrovirus DNA sequence termed (LTR) the long terminal repeat plus additional retrovirus sequences. The model system for the general process described in LTR vector plus a gene with transforming potential. As indicated below, the retroviruses are an ideal model system because they contain transduced cellular sequences (ONC) homologous to DNA sequences in mammalian cells. The viral homolog of this (V-ONC) sequence is known to be transforming, i.e., to induce neoplasia. The cellular homolog of the viral sequence (C-ONC) is non-transforming. The significance of this is that inactive cellular genes were activated when naturally transduced into a retrovirus.

The following detailed description discusses the preparation of the vectors, transfection, transformation and rescue of the DNA sequence for the retrovirus model.

The implication of this is that a retrovirus can be used to clone cellular sequences. This experiment could have been performed with any cell DNA fragment for which a selectible marker exists, for example, thymidine kinase. We have shown that the LTR alone is capable of activating the transforming potential of a particular ONC sequence C-mos even when located some distance from it. The retrovirus vector in (5' LTR plus additional information including gag) may also be able to transduce other genes permitting the generation of a retrovirus gene library by covalently linking partially digested cellular DNA to a retrovirus vector.

The model system detailed below describes recombinant DNA clones comprised of the LTR vector and a transforming sequence. In this system the appearance of foci in cells transfected with DNA is the identifiable phenotype. Individual foci can be superinfected with helper virus giving rise to rare infectious transforming viruses. The mechanisms for the generation of a complete virus from a recombinant lacking certain viral sequences are not known. Secondary foci generated by this new complete transforming virus yield high levels of the virus. The rescue allows the complete purification of the gene of interest. The rescued virus can then be used as a source of the gene of interest for more conventional cloning by recombinant DNA technology.

Retroviruses

Retroviruses are RNA viruses that replicate through DNA intermediates and an obligatory step in their life cycle is integration of a DNA intermediate into the host genome.

In infected cells the DNA intermediates (unintegrated provirus) become stably associated with the host chromosome via an as yet uncharacterized integration process to form the provirus.

Particularly of interest are those avian and mammalian retroviruses which rapidly produce a variety of neoplasias in host animals. (The much studied leukemia viruses are slow to produce tumors.) Bishop, J. M. (1978) Ann. Rev. Biochem. 47, 35–88; Weinberg, R. A. (1980) Ann. Rev. Biochem. 49, 197–226; Fischinger, P. J. (1979) in Molecular Biology of RNA Tumor Viruses (Stephenson, J. R. ed.), pp. 163–198, Academic Press, N.Y.; Duesberg, P. H. (1979) Cold Spring Harbor Symp. Quant. Biol. 44, 13–29). Most of these viruses are defective and lack a full complement of retrovirus replication genes, but they possess specific sequences that are homologous to sequences in the host genome. These sequences are presumably transduced from the normal genetic information of the host and there is overwhelming evidence correlating their expression in the provirus with the transforming phenotype. These sequences are highly conserved unique sequences in avian and mammalian cell DNA. (ibid.)

Until very recently, rigorous studies of the structure of the genomes of these viruses were hampered by the lack of sufficient quantities of intact viral RNA and restricted to those few viruses that are produced in abundance in tissue culture. With the advent of molecular cloning these limitations are eliminated and all of the molecular biological techniques developed for analyzing DNA can be easily applied to the cloned proviral DNA.

Application of molecular cloning techniques to retroviruses provides a means for studying the structures of both integrated and unintegrated proviruses and thereby indirectly the study of the mechanism of integration itself. These analyses gave the first direct evidence that retroviruses resemble prokaryote and eukaryote transposable elements. (Shimotohno, K., Mizutani, S. and Temin, H. (1980) Nature 285, 550–554; Sutcliffe, J. G., Shinnick, T. M., Verma, I. M. and Lerner, R. A. (1980) Proc. Nat. Acad. Sci. U.S.A. 77, 3302–3306; Dhar, R., McClements, W. L., Enquist, L. W. and Vande Woude, G. F. (1980) Proc. Nat. Acad. Sci. U.S.A. 77, 3337–3941; and Shoemaker, C., Goff, S., Gilboa, E., Paskind, M., Mitra, S. W. and Baltimore, D., Proc. Nat. Acad. Sci. U.S.A. 77, 3932–3936.)

One of the most powerfule applications of recombinant DNA technology to retroviruses has been to provide a means for studying and identifying the essential genetic elements that contribute to oncogenic transformation. (Oskarsson, M., McClements, W. L., Blair, D. G., Maizel, J. V. and Vande Woude, G. F. (1980) Science 107, 1222–1224; Blair, D. G., McClements, W. L., Oskarsson, M., Fischinger, P. J. and Vande Woude, G. F. (1980) Proc. Nat. Acad. Sci. U.S.A. 77, 3504–3508; McClements, W. L., Dahr, R., Blair, D. G., Enquist, L. W., Oskarsson, M. K., and Vande Woude, G. F. (1980) Cold Spring Harbor Symp. Biol. 45, in press; Chang, E. H., Maryak, J. M., Wei, C. M. Shih, T. Y., Shober, R., Cheung, H. L., Ellis, R., Hager, G., Scolnick, E. M. and Lowy, D. R. (1980) J. Virol. 35, 76–92).

The genomes of sarcoma retroviruses contain sequences acquired from the host cell which are a prerequisite for their tumoriogenic potential and their ability morphologically to transform cells in vitro. These sequences have been isolated using recombinant DNA cloning techniques. These acquired sequences are termed V-ONC. The V-ONC sequences were acquired during putative recombination between parental leukemia virus and host cell information. To date, about 14 cellular sequences with transforming potential have been identified as materially transduced retrovirus sequences. This may be thought of as spontaneous rescue of a cellular sequence. They are extremely rare events in nature.

Most of these acute transforming viruses lack replication functions and require helper retrovirus functions to be packaged into infectious particles. The Moloney murine sarcoma virus (MSV) arose spontaneously during passage of Moloney murine leukemia virus (MuLV) in Balb/c mice and contains both MuLV and normal Balb/c mouse cell sequences. The mechanism by which the viral acquired cellular sequence (v-mos) participate in cell transformation is unknown. Likewise, the physiological function of the normal cell c-mos (normal cell DNA sequences homologues to v-mos) is unknown.

A comparative analysis of the physical and biological properties of c-mos and v-mos by cloning in phage λ was made. The c-mos region is indistinguishable from the v-mos region as judged by heteroduplex and restriction endonuclease analyses. The cellular sequences flanking c-mos show no homology to other Moloney sarcoma virus sequences. Whereas cloned subgenomic portions of Moloney sarcoma virus that contain mos$^M$ transformed N1H3T3 cells in vitro, the cloned c-mos fragment is inactive. (Oskarsson, M., McClements, W. L., Blair, D. G., Maizel, J. V. and Vande Woude, G. F. (1980) Science 107, 1222–1224).

Investigation of the sequences flanking v-mos is of importance for its tumorigenic potential and its integration into the cell DNA.

The terminal retroviral sequences are referred to as long terminal repeats (LTR).

Briefly, the LTR is composed of unique sequences derived from both the 5' ($U^5$) and 3' ($U^3$) ends of genomic viral RNA. (Gilboa, E., S. Goff, A. Shields, F. Yoshimura, S. Mitra, and D. Baltimore (1979) Cell 16:863; Gilboa, E., S. Mitra, S. Goff, and D. Baltimore (1979) Cell 18:93.) For Moloney murine leukemia virus (M-MLV) a short, terminally repeated RNA sequence (R). (Coffin, J. M., T. C. Hageman, A. M. Maxim, and W. A. Haseltine (1978) Cell 13:761), enables $U^5$ sequences to be translocated to the opposite terminus during proviral DNA synthesis. The resulting LTR has the structure $U^3RU^5$.

We have investigated some of the properties of a retrovirus LTR using the molecularly cloned, integrated proviruses of the m1 and HT1 strains of Moloney sarcoma virus (MSV). (Vande Woude, G. F., M. Oskarsson, L. W. Enquist, S. Nomura, M. Sullivan, and P. J. Fischinger (1979) Proc. Natl. Acad. Sci. 76:4464; Vande Woude, G. F., M. Oskarsson, W. McClements, L. Enquist, D. Blair, P. Fischinger, J. Maizel and M. Sullivan (1980) Cold Spring Harbor Symp. Quant. Biol. 44:753), and have determined the nucleotide sequences of both 588-base-pair (bp) LTR elements of integrated m1MSV and adjacent host DNA. (Dhar, R., W. McClements, L. Enquist, and G. F. Vande Woude (1980)

Proc. Natl. Acad. Sci. 77:3937.) Three characteristic features of LTR emerged from the DNA sequence. First, each LTR has 11-bp inverted terminal repeat sequences (5'TGAAAGACCCC), and since the LTR elements are direct repeats, the provirus itself has inverted terminal repeats. It seems likely that these inverted repeats are critical sequences for integration (ibid.). Second, the m1MSV has a direct 4-bp repeat of host DNA at the provirus-host junctions. Third, within the LTR sequence there are putative RNA transcription control signals (ibid.). These three features of LTR are also found in prokaryote insertion sequence (IS) elements. Furthermore, the general structure of the integrated provirus is similar to some bacterial transposons (ibid. and McClements, W. L., L. W. Enquist, M. Oskarsson, M. Sullivan, and G. F. Vande Woude (1980) J. Virol. 35:488).

The derivation of pm1sp, pRC1, pRC3, vectors 1, 2 and 3 respectively, are given below.

Plasmid pm1sp vector 1 contains one copy of the m1 MSV LTR plus the host flanking sequences surrounding integrated m1 MSV. This eukaryotic sequence is inserted into the Eco RI site of pBR322. The MSV sequences were obtained from a spontaneous deletion mutant of λ m1 in which homologous recombination between the two LTR sequences has excised all the unique MSV information between the two LTRs. The resultant Eco RI insert in the deleted λ phage was transferred to the Eco RI site of pBR322. Detailed descriptions of this deletion mutant and pm1sp are found in McClements, et al., (1980) *Journal of Virology* 35, 488–497; and McClements, et al., (1981) Cold Spring Harbor Symposium on Quantitative Biology 45, in press.

Plasmids pRC1, vector 2, and pRC3, vector 3 were derived from m1 MSV sequences. Plasmid pRC1 contains MSV information from the left LTR to the Sma I site immediately preceding v-mos; it also contains the left host flanking sequence. (See FIG. 2 and McClements et al., *J. Virology* 35, 488–497, FIG. 1.) pRC1 was generated by partial Sma I and complete Eco RI digestion of a derivative of m1. The appropriate partial Sma I digest fragment (≈3200 bp) was purified by agarose gel electrophoresis inserted into plasmid pBR322 between the Eco RI and Pvu II sites.

Figure 2:
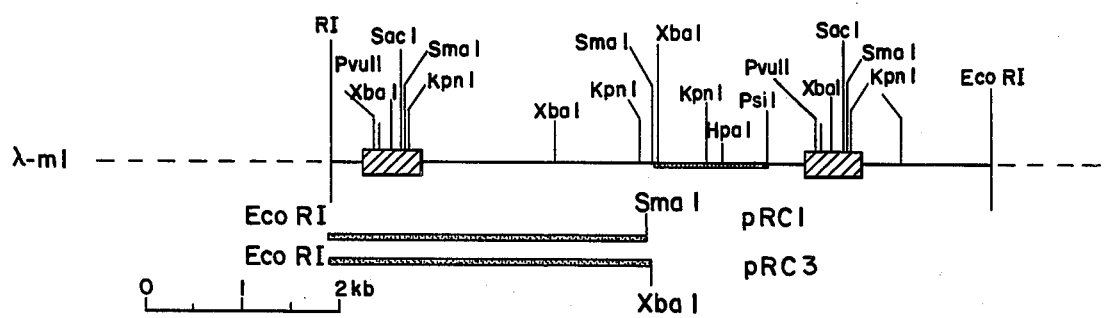
Figure 2:
Figure 2:
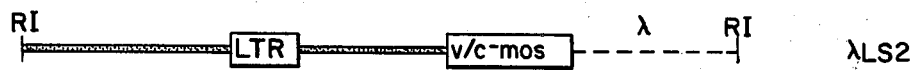
Figure 2:
Figure 2:
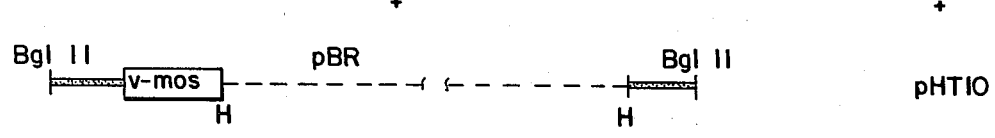
Figure 2:

Plasmid pRC3 contains a similar m1 MSV sequence, but it extends from the left Eco RI site to the Xba I site immediately preceding v-mos (FIG. 2). This m1 MSV sequence was generated by partial Xba I and complete Eco RI digestion. The resulting fragment was purified and inserted into the Eco RI and Xba I sites of plasmid pA10. pA10 is a derivative of pBR322 in which an Xba I linker sequence was inserted between the Eco RI and Bam HI sites.

We have demonstrated that the MSV LTR element has two unique but related biological activites. First, it stimulates transformation by v-mos sequences of MSV in a direct DNA transfection-transformation assay. Second, the transforming potential of the normal mouse c-mos sequence has been activated by linking MSV sequences containing an LTR to c-mos DNA.

Activation of c-mos Transformation by LTR

We have demonstrated that the molecularly cloned c-mos region in λ MC-mos is identical to the v-mos of HT1 and m1 MSV by heteroduplex and restriction endonuclease mapping. However, λ MC-mos and a subclone containing c-mos (pMS$_1$) were inactive in the transformation assay (Table 1). The difference in activity of cloned c-mos and v-mos has been attributed to their adjacent sequences. The active v-mos has M-MLV sequences adjacent to it, whereas inactive c-mos has normal cellular sequences adjacent to it. We, therefore, constructed a recombinant (λ LS$_1$; Table 1) between c-mos and pHT13 yielding a structure similar to pHT21. Replacing the cellular sequences to the 3' side of c-mos with MSV-derived sequences including an LTR did not generate an efficient transforming sequence. However, λ LS$_2$, generated by replacing cellular sequences preceding (5' to ) c-mos with M-MLV sequences derived from m1 MSV (Table 1) causes c-mos to transform cells with about the same efficiency as an analogous subgenomic clone of λ HT1.

TABLE 1

| Clone Designation | LTR Activation of c-mos Transforming Potential Schematic of fragment tested[a] | Activity[b] (ffu/pmole DNA) |
|---|---|---|
| | R B$_2$ X B$_1$    H B$_2$ R | |
| 1. λMC-mos | — — — — . . . . . — — — — — | n.d. |
| 2. pMS$_1$ | — — — . . . . - | n.d. |
| 3. λLS$_1$ | — — — — . . . x___ooo . . . / / . . . | 3 |
| 4. λLS$_2$ | . . ooo___x . . . | 2700 |
| 5. pMSB$_7$[c] | - < > - . . . . . - | n.d. |
| 6. pTS$_1$ | . . ooo > - . . . . . - | 6900 |

[a]Symbols:
(— — —) normal mouse sequences flanking the c-mos (Oskarsson et al. 1980);
(. . . .) c-mos sequences (Oskarsson et al. 1980);
(< >) sequences deleted by Bal 31 digestion;
(. . . .) normal mink sequences flanking the integrated provirus ___;
(ooo) LTR;
(___) MSV sequences derived from M-MLV;
and M-MLV (xxxx) v-mos sequences.
Restriction endonuclease sites used for subcloning and generating recombinants are indicated: (R)EcoRI; (B$_2$)BglII; (X)XbaI; (B$_1$)BglII; and (H)HindIII.
[b]DNA was transfected onto NIH-3T3 cells (see below).
[c]pMS$_1$ was digested with XbaI and then exonuclease Ba131. With approximately 600 bp of normal mouse sequences remaining 5' to c-mos, the plasmid was either reclosed to generate mPSB$_7$ or part of the m1M-MuSV LTR was ligated to the remaining normal mouse sequences approximately 600 bp from the 5' end of c-mos to generate pTS$_1$.

To eliminate any possible contribution of non-LTR M-MuLV sequences to the activation of c-mos, a recombinant was constructed between c-mos and part of the LTR. This clone pTS$_1$, contains mlMSV LTR sequences from pmlsp linked to cellular sequences about 600 bp preceding the 5' end of c-mos. Plasmid pTS$_1$ transforms with a specific activity equivalent to pHT21 or pHT25. The clone from which c-mos sequences in pTS$_1$ were derived and a control subclone lacking LTR do not cause transformation. Therefore, the LTR alone is responsible for activating a normally quiescent cellular DNA sequence.

The experiments we describe demonstrate that cloned MSV proviral DNA transforms normal cells efficiently in a DNA transfection assay and that the transformed cells contain a rescuable MSV genome. In addition, we show that leukemia sequences appear to enhance the transforming efficiency of MSV v-mos containing fragments.

EXPERIMENTAL PROCEDURES

Viruses and Cells

A cloned line of N1H3T3 cells, described by Andersson et al. (Anderson, P., Goldfarb, M. P. and Weinberg, R. A. (1979) Cell 16, 63–75), and obtained from L. Turek (National Cancer Institute) was grown in Dulbecco's modified minimal essential medium (GIBCO) supplemented with 10% (vol/vol) calf serum and antibiotics. 3T3 F1 cells, mink lung cells (CCL64), and feline embryo fibroblasts (FEF) were maintained on McCoy's 5a modified medium (GIBCO), supplemented with 15% (vol/vol) fetal calf serum and antibiotics. Assays for sarcoma and leukemia viruses were performed on these cells as described (Bassin, R. H., Tuttle, N. and Fischinger, P. J. (1971) Nature (London) 229,564–566; Fischinger, P. J., Blevins, C. S., and Nomura, S (1974) J. Virol. 14, 177–179). MSV was rescued by infecting cells with the IC clone of Moloney murine leukemia virus (MLV) (Fischinger, P. J., Moore, C. O. and O'Conner, T. E. (1969) J. Natl. Cancer Institute 42, 605–622) at a multiplicity of 0.1–1 infectious virus per cell.

Isolation and Characterization of Recombinant Clones

The isolation of the ml and HT1 MSV genomes from transformed mink cells and their subsequent cloning in the EK2 vector lambda gt WES-lambda B have been described (Vande Woude, G. F., Oskarsson, M., Enquiest, L. W., Nomura, S., Sullivan, M. and Fischinger, P. J. (1979) Proc. Natl. Acad. Sci. USA 76, 4464–4468; Vande Woude, G. F., Oskarsson, M., McClements, W. L., Enquist, L. W., Blair, D. G., Fischinger, P. J., Maizel, J. V., and Sullivan, M. (1979) Cold Spring Harbor Symp. Quant. Biol., in press). These recombinants have been designated λ ml and λ HT1, respectively. Both ml MSV and HT1 MSV were originally derived from a tumor-inducing uncloned MSV stock (Moloney, J. B. (1966) Natl. Cancer Inst. Monogr. 22, 139–142). The ml MSV genome codes for a specific polyprotein pP$_{60}$ gag (Robey, W. G., Oskarsson, M. K., Vande Woude, G. F., Naso, R. B., Arlinghaus, R. B., Haapala, D. K. and Fischinger, P. J. (1977) Cell 10, 79–89) whereas HT1 does not specify any detectable virus-coded protein (ibid.). FIG. 1 shows a schematic representation of the MSV regions used in these transfection studies. These were subcloned in the EK2 plasmid vector pBR322 (Bolivar, R., Rodriguez, P., Greene, P., Bellach, M., Heynecker, H., Boyer, H., Crassa, J. and Falkow, S. (1977) Gene 2, 95–113). The cloned fragments are shown approximately to scale and are compared to the intact ml and HT1 MSV proviral genomes. Plasmid and λ recombinant DNA was extracted, purified, and analyzed by agarose gel electrophoresis after restriction endonuclease digestion (Vande Woude, G. F., Oskarsson, M., Enquist, L. W., Nomura, S., Sullivan, M. and Fischinger, P. J. (1979) Proc. Natl. Acad. Sci. USA 76, 4464–4468; Vande Woude, G. F., Oskarsson, M., McClements, W. L., Enquist, L. W., Blair, D. G., Fischinger, P. J., Maizel, J. V. and Sullivan, M. (1979) Cold Spring Harbor Symp. Quant. Biol., in press).

FIG. 1 is a physical map of Moloney murine sarcoma virus (MSV) derived hybrids. The simplified maps of the integrated provirus EcoRI fragments (λ ml and λ HT1) are shown indicating the gag and v-mos$^M$ regions (▨), terminally redundant sequences (LTR) (▱), and mink host flanking sequences (hf). Pertinent restriction endonuclease sites are shown: R, EcoRI; Xb, Sba, I, S, Sac I; B, Bgl II; Xh, Xho I; H, HindIII. Below the λ ml (and λ HT1) line a physical map are maps of the cloned subgenomic fragments derived from λ ml (or λ HT1). The specific sequences subcloned in each case are indicated on the map. All subcloning was done in plasmid pBR322. Restriction fragments of λ ml and λ HT1 were either cloned directly or first purified by preparative agarose gel electrophoresis.

Plasmids pm 15 line b and pm 13 line c were made from a Bgl II digest of purified λ ml EcoRI insert cloned into the EcoRI and BamHI sites of pBR322. Plasmid 13 is a plasmid of LTR and v-mos with good transforming efficiency.

Plasmid mplsp line d contains only one copy of the LTR and the mink sequences flanking the ml MSV integration site. It was made from an EcoRI digest of EcoRI λ mlr+, a deletion isolate of λ ml in which the unique MSV sequences and one LTR have been lost.

Plasmids pHT10 and pHT11 line f are identical, independently derived clones of the 2.1-kb HindIII fragment of v-mos λ HT1.

Plasmids pHT15 line h and pHT13 line g were generated by HindIII digestion of the purified EcoRI insert of λ HT1 and cloned into the HindIII and EcoRI sites of pBR322.

Partial HindIII digestion of the same EcoRI fragment allowed construction of pHT25, line k. Transforming efficiency is very high.

Plasmids pHT21 line i and pHT22 line j were made in vitro by cloning the Bgl II/HindIII MSV specific fragments of pHT10 into pHT13, which had been cut with HindIII plus BamHI to ensure correct orientation of the insert. All subclones have been characterized by restriction mapping. Here too, transformation was high.

Plasmids shown in lines c, i, j and k gave high transformation efficiencies. The readily apparent similarity of all these plasmids is that the genome in each instance is joined to an LTR.

DNA Transfection Assays

The DNA transfection of NIH3T3 cells ($2.5 \times 10^5$ cells per 35-mm culture dish) was performed by modifications of established procedures (Lowry, D. R., Rands, E. and Scolnick, E. M. (1977) J. Virol 26, 291–298; Graham, F. L. and Van Der Eb, A. J. (1973) Virology 52, 456–467; and Stowe, N. D. and Wilkie, N. M. (1976) J. Gen. Biol. 33, 447–458). Calf thymus DNA (Worthington, lot 38N687P), sheared by passing it 10 times through a 23-gauge needle, was present in all transfections at 40 μg/ml. The cells were trypsinized ≈18 hr after DNA treatment and distributed to three 60-mm dishes. The medium was changed at 2- to 3-day intervals, and foci were scored 12-16 days after transfer.

Transforming Activity of Moloney ml and HT1 Proviral Genomes

The EcoRI-restricted fragments from λ ml and λ HT1, which contained the integrated ml and HT1 proviral genomes, were used to transfect mink lung (CCL64) and cat (FEF) cells. The ml and HT1 MSV proviral DNA produced transformed foci on these cells at low efficiency [~16 focus-forming units (FFU)/μg of MSV DNA], but focus formation was dependent on the addition of replicating leukemia helper virus (not shown). We also found that these cells were much more susceptible to DNA transfection and that helper-independent focu were readily detectable. In these cells, focus formation was dependent on the amount of MSV DNA added; the number of foci induced varied linearly with the amount of added DNA at levels below 0.1-0.2 g. Above this level the addition of more DNA resulted in either no increase or a slight reduction in the number of foci observed. Both the intact provirus and the v-mos containing subgenomic fragment in pm13 gave approximately 1-hit dose-response for focus formation. Under standard assay conditions, EcoRI-digested λ ml DNA fragments have a specific activity of $1.1 \times 10^4$ FFU/μg of MSV proviral DNA.

The exact role that LTR plays in transfection is not certain. The LTR contains a promoter-like sequence with the same polarity as the viral genome; and could act to promote efficient transcription of v-mos. LTR could also act to cause the efficient integration of proviral DNA. If so, LTR could be functioning in an analogous fashion both in transfection and in viral infection.

Transforming Activity of Cloned Subgenomic Fragments of MSV

We examined the ability of cloned subgenomic fragments to induce foci on NIH3T3 cells (Table 2) at two or more DNA concentrations. Subcloned fragments lacking v-mos sequences (related to line b, line d, line g and line h, see FIG. 1) were unable to induce cell transformation. Similar amounts of the pm13 line c fragment, containing the entire 3' half of the ml MSV genome, induced foci with an efficiency reduced to one-sixth that of the entire ml MSV provirus. Thus, removal of leukemia sequences in the 5' half of the MSV genome only slightly reduced cell transformation. However, pHT10 and pHT11, line f two independently isolated clones containing the internal 3.0-5.2-kb HindIII fragment from λ HT1 and all of the apparent v-mos information found in ml MSV, transformed cells with a markedly reduced efficiency. Repeated assays using between 100 ng and 2 μg of these cloned DNAs either failed to induce any foci or, at most, induced one or two foci which frequently exhibited atypical morphology. Mixing experiments with ml MSV DNA indicated the MSV sequences from pHT10 and pHT11 did not inhibit transformation. The average efficiency of these two fragments, more than 1/1000th that of pm13, suggested that sequences to the 3' side of the v-mos region enhanced transformation efficiencies.

To test this hypothesis, we rejoined the pHT10 MSV sequences (low transformation efficiency) to the 3'MSV (leukemia-derived) sequences contained in pHT13 (non-transforming), generating the clones pHT21 and pH22 (line i and j). The MSV fragments in these clones differ only in the amount of leukemia-related information that is 5' to the v-mos sequence. Both regenerated fragments transformed 1000-fold more efficiently than their pHT10 parent and exhibited the same transforming efficiency as pm13. However, the MSV fragment present in the λ HT1-derived clone pHT25, which lacked the leukemia sequences 3' to v-mos present in pHT21 and 22 but which contained the entire 5' half of HT1 MSV (0-5.2 kb) (see FIG. 1), transformed with the same efficiency as the pm13, pHT21, and pHT22 MSV fragments. Thus, although the MSV sequences contained in pHT10 transformed inefficiently, the presence of additional leukemia and mink flank sequences derived from either the 5' or 3' portions of the cloned MSV proviral genome stimulated the transforming efficiency 1000-field. Aside from the 3.8- to 5.2-kb leukemia v-mos region, FIG. 1 reveals that the 600-base-pair LTR is the only sequence obviously common to all three clones that transform with high efficiencies. Moreover, we have determined that cotransfection of pHT10 and pmlsp (line d and f mixed) stimulates the transforming efficiency of pHT10 300-fold. These experiments have been described in more detail in McClements et al. Cold Spring Harbor Symposium 1980, but one example is given to Table 2. The mp1sp contains the mink flank sequences and one copy of the LTR. Collectively, these experiments suggest that LTR is responsible for the enhanced transformation efficiency.

Rescuability of MSV From Transfected Cells and Expression of MSV-Coded Proteins

Cell cultures derived from individual ml and HT1 MSV-induced foci were examined for MSV-coded protein expression and were infected with leukemia virus to determine MSV rescuability. Most, but not all, foci induced by transvection with the intact cloned provirus could be rescued and transformed cell subclones isolated from these foci, with few exceptions, were also rescuable. We observed that the number and rate of appearance of MSV foci were enhanced by superinfection with MLV. Foci were obtained as early as 5 days after transfection when MLV was added, in contrast to the 10-13 days required in the absence of helper.

The ml MSV genome specifically codes for a defective gag polyprotein (pP60$^{gag}$) containing MLV p30 determinants, whereas HT1 MSV does not specify any known virus-coded protein. Double fluorescent antibody analysis of cells transfected with EcoRI-digested λ ml and λ HT1 showed that at least half of the foci induced by ml MSV contained cells expressing p30 antigenic determinants, whereas cells transformed by HT1 MSV were negative, λ ml and λ HT1 MSV virus could be rescued from cells transformed by λ ml and λ HT1 DNA, respectively. (Table 2)

Rescue of transforming viruses from cells transfected by subgenomic fragments, λLS2 and pHT25 has also been shown (FIG. 2). λ LS2 consists of the 5' portion of MSV covalently linked to the c-mos cell gene and transforms cells with high efficiency. Individual foci produced by this subgenomic fragment, when superinfected with M-MLV helper virus releases an infectious transforming virus at low efficiency. Secondary foci generated by this transforming virus yield virus of high titer.

TABLE 2

| Specific Infectivity of Cloned Whole and Partial Genomes of MSV | | |
|---|---|---|
| Related to FIG. 1 | Source of MSV Sequences* | Specific Infectivity+ |
| line a | ml** | 46,000 ± 15,000 whole genome |

TABLE 2-continued

Specific Infectivity of Cloned Whole and Partial Genomes of MSV

| Related to FIG. 1 | Source of MSV Sequences* | Specific Infectivity+ | | |
|---|---|---|---|---|
| line a | HT1** | 37,000± | 28,600 | whole genome |
| line c | pm13 | 8,100± | 4,100 | LTR-vmos$^M$ |
| line f | pHT1o | 7± | 7 | vmos$^M$ |
| line f | pHT11 | | 20 | vmos$^M$ |
| line g | pHT13 | | 1 | LTR |
| line i | pHT21 | 6,900± | 1,400 | LTR-vmos$^M$ |
| line j | pHT22 | 8,100± | 400 | LTR-vmos$^M$ |
| line k | pHT25** | 7,800± | 2,500 | LTR-vmos$^M$ |
| line b | pm15 | | 4 | LTR |
| line d | pm1sp | | 4 | LTR |
| line h | pHT15 | | 12 | LTR |
| line d & f | pHT10 and pm1sp‡ | 2,100± | 700 | Mixture of LTR and vmos$^M$ (not joined) |

*The MSV region derived from each clone is shown in FIG. 1.
+Given in FFU/pmol. The mean± SD of n determinations (in parentheses) are given for each clone.
‡Mixtures containing 0.25 μg of each cloned DNA were precipitated and assayed.
**Superinfection with MM1V rescued infectious transforming virus in these cells.

TABLE 3

| | Cloned Transfected | HT25 | LS2 | pRC1 and pH10 or pHT10 | pRC1 and pHT10 |
|---|---|---|---|---|---|
| 1. | specific infectivity | 7800 °ffu/p mole DNA | 2,700 ffu/p mole DNA | cotransfected* 400 ffu/p mole mos DNA | litaged 670 ffu/p mole mos DNA |
| 2. | viral antigen expression | p30, gp70 | p30 + gp70 − | p30 + (11/19) | p30 + (⅛) |
| 3. | rescue; infectious focus forming activity | | | | |
| | a. number | 9/33 | 4/6 | 7/17 | 6/9 |
| | b. titer (original) | 2-30 ffu/ml | 8 × 10$^2$ ffu/ml | 10-20 ffu/ml | 4-50 ffu/ml |
| | c. titer (secondary) | 10$^3$-10$^5$ ffu/ml | 3/10$^4$ ffu/ml | 6/10$^2$ ffu/ml | 10$^3$ ffu/ml |
| | d. viral RNA | 7,400 bases; mos +, pBR + | 6,100 bases; mos +, pBR 4,700 bases; mos +, pBR | n.t. | n.t. |

°ffu = focus forming units
n.t. = not tested

Subgenomic fragment pHT25, similar to λ LS2, but containing v-mos also transforms cells. Superinfection of foci generated by pH25 with M-MLV allows rescue of a transforming virus that can be amplified.

These results are summarized in Table 3. Designation 1 (specific activity) gives the number of focus-forming units per pico-mole of DNA. Designation 2 shows expression of viral genes other than v-mos. In rescue, marked 3, a shows the number of successful rescues out of a total number of attempts. Section b gives titer of virus from original foci and section c titer of virus from cells infected with virus in b. In d, the composite of genomic RNA in rescued virus is given.

The model system is designed to show that a vector containing 5' retroviral information in addition to the LTR could be used to generate rescuable retroviruses containing any selectable marker. Two such LTR vectors were generated from ml MSV designated pRC1 and pRC3 (FIG. 2). Table 3 shows the rescue results for pRC1 plus pHT10, either cotransfected (mixed) or ligated (linked). As shown in FIG. 2, plasmid pHT10 was opened at the Bgl II site and plasmid pHT10 was opened at the BamHI site. In both the co-transfected and ligated cases, a transforming rectovirus was rescued and was shown to be infectious by replication to high titer.

We claim:

1. A process for activating the expression of any gene comprising the steps of:
   (a) isolating the gene
   (b) ligating to the gene a vector comprising the LTR sequences from a retroviral provirus genome to provide a hybrid gene
   (c) inserting the hybrid gene into a mammalian recipient cell using DNA transfection
   (d) screening for the phenotype of the gene.

2. A process of claim 1 wherein the vector is derived from ml Moloney sarcoma virus.

3. A process of claim 2 wherein the vector is selected from the group consisting of pm1sp, pRC1 and pRC3.

4. A process of claim 1 wherein in step (b) the gene and vector are transfected together.

5. A process for activating the expression of a transforming gene comprising the steps of:
   (a) isolating a transforming gene,
   (b) ligating to the gene a vector comprising the LTR sequences from a retroviral provirus genome to produce a hybrid gene,
   (c) inserting the hybrid gene into a mammalian recipient cell using DNA transfection,
   (d) screening for the morphologic phenotype of the activated transforming gene.

6. A process of claim 5 wherein the vector is derived from ml Moloney sarcoma virus.

7. A process of claim 6 wherein the vector is selected from the group consisting of pm1sp, pRC1 and pRC3.

8. A process of claim 5 wherein in step (b) the gene and vector are co-transfected.

9. A process for activating, cloning and rescuing any gene comprising the steps of:
   (a) isolating a gene,
   (b) ligating the gene to the vector pRC1 or pRC3 to form a hybrid gene,
   (c) inserting the hybrid gene into a mammalian recipient cell using DNA transfection,
   (d) screening for the phenotype of the gene,
   (e) isolating individual cell populations,
   (f) infecting these populations with helper virus and achieving a low yield of secondary clones containing the activated gene,
   (g) using the secondary clones to produce virus containing the activated gene in high, usable yield.

10. A process for activating, cloning and rescuing in the form of an infectious retrovirus any transforming gene comprising the steps of:
    (a) isolating a transforming gene,
    (b) ligating the gene to the vector pRC1 or pRC3 to form a hybrid gene,
    (c) inserting the hybrid gene into a mammalian recipient cell using DNA transfection, (d) screening for the morphological phenotype of the activated transforming gene,
(e) isolating individual morphologically transformed cell populations,
(f) infecting these populations with helper virus and obtaining cell culture media from individual infected cell populations which contain infectious transforming virus,
(g) amplifying the number of infectious transforming virus particles by infection of susceptible cells to obtain a preparation of viruses containing the activated gene in high, usable yield.

* * * * *